United States Patent [19]
Baldwin et al.

[11] Patent Number: 5,438,055
[45] Date of Patent: Aug. 1, 1995

[54] ANTIARRHYTHMIC BENZODIAZEPINES

[75] Inventors: John J. Baldwin, Gwynedd Valley; Jason M. Elliott, Blue Bell; David A. Claremon, Maple Glen; Nigel Liverton, Harleysville; David C. Remy, North Wales; Harold G. Selnick, Ambler, all of Pa.

[73] Assignee: Merck & Co., Inc., Rahway, N.J.

[21] Appl. No.: 156,183

[22] Filed: Nov. 22, 1993

[51] Int. Cl.$^6$ .............................. A61K 31/55
[52] U.S. Cl. ...................... 514/221; 514/821
[58] Field of Search ............ 514/212, 221, 821; 540/509

[56] References Cited

U.S. PATENT DOCUMENTS

| | | | |
|---|---|---|---|
| 4,820,834 | 4/1989 | Evans et al. | 540/504 |
| 5,166,151 | 11/1992 | Freidinger et al. | 514/215 |
| 5,264,432 | 11/1993 | Rüger et al. | 514/220 |
| 5,302,591 | 4/1994 | Fletcher et al. | 514/221 |
| 5,324,726 | 6/1994 | Bock et al. | 514/221 |

FOREIGN PATENT DOCUMENTS

| | | |
|---|---|---|
| 0514133A1 | 11/1992 | European Pat. Off. |
| 0538945A1 | 4/1993 | European Pat. Off. |
| 93/02078 | 2/1993 | WIPO |
| 93/07131 | 4/1993 | WIPO |
| 93/08176 | 4/1993 | WIPO |
| 93/17011 | 9/1993 | WIPO |
| 93/19063 | 9/1993 | WIPO |

OTHER PUBLICATIONS

Remington's Pharmaceutical Sciences, 16th edition (1980) pp. 420–435.
U.S. Patent Application 07/992,217, Chambers, 12/92.
U.S. Patent Application 08/139,254, Chambers et al., 10/93.
U.S. Patent Application 08/156,331, Baldwin et al. 11/93.
U.S. Patent Application 08/155,670, Baldwin et al. 11/93.
U.S. Patent Application 08/155,672, Bock et al. 11/93.
U.S. Patent Application 08/155,669 Baldwin et al. 11/93.

*Primary Examiner*—Raymond Henley, III
*Attorney, Agent, or Firm*—Sylvia A. Ayler; Francis P. Bigley; Mark R. Daniel

[57] ABSTRACT

Benzodiazepine derivatives with an amide or urea function in the 3-position are useful in the treatment of arrhythmia. The compounds have structural formulae:

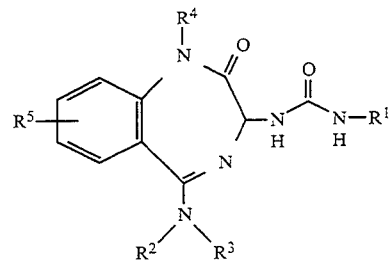

4 Claims, No Drawings

ANTIARRHYTHMIC BENZODIAZEPINES

SUMMARY OF THE INVENTION

This invention is concerned with a novel method of treating arrhythmia by the administration of a compound of general structural formula I:

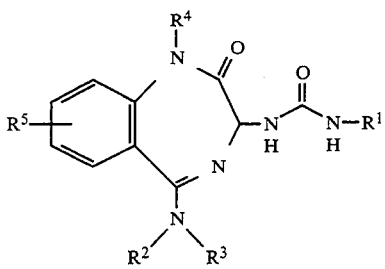

The invention is also concerned with pharmaceutical formulations comprising one or more of the compounds as active ingredient, either alone or in combination with one or more of a Class I, Class II or Class IV antiarrhythmic agent.

BACKGROUND OF THE INVENTION

Arrhythmias often occur as complications to cardiac diseases such as myocardial infarction and heart failure. In a serious case, arrhythmias give rise to a ventricular fibrillation and can cause sudden death.

Though various antiarrhythmic agents are now available on the market, those, having both satisfactory effects and high safety, have not been obtained. For example, antiarrhythmic agents of Class I according to the classification of Vaughan-Williams which cause a selective inhibition of the maximum velocity of the upstroke of the action potential (Vmax) are inadequate for preventing ventricular fibrillation. In addition, they have problems regarding safety, namely, they cause a depression of the myocardial contractility and have a tendency to induce arrythmias due to an inhibition of the impulse conduction. Beta-adrenoceptor blockers and calcium antagonists which belong to Class II and IV respectively, have a defect that their effects are either limited to a certain type of arrhythmia or are contraindicated because of their cardiac depressant properties in certain patients with cardiovascular disease. Their safety, however, is higher than that of the antiarrhythmic agents of Class I.

Antiarrythmic agents of Class III are drugs which cause a selective prolongation of the duration of the action potential without a significant depression of the Vmax. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drugs of this class are expected to be effective in preventing ventricular fibrillations. Pure Class III agents, by definition, are not considered to cause myocardial depression or an induction of arrhythmias due to the inhibition of the action potential conduction as seen with Class I antiarrhythmic agents.

DETAILED DESCRIPTION OF THE INVENTION

The novel method of treating arrhythmia of this invention comprises the administration to a host animal (including human) in need of such treatment of an effective amount of a compound with structural formula I:

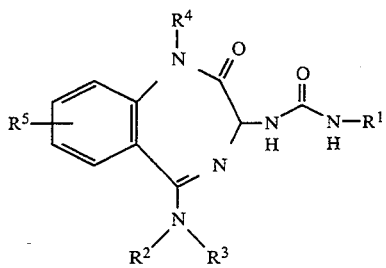

or a pharmaceutically acceptable salt thereof, wherein
$R^1$ is
1) phenyl, either unsubstituted or substituted with one or two substituents selected from Cl, F, $CF_3$, $C_{1-3}$ alkyl and $C_{1-3}$ alkoxy,
2) indan-5-yl;
$R^2$ and $R^3$ are independently
1) $C_{1-3}$ alkyl, either unsubstituted or substituted with phenyl, or
2) $C_{3-7}$ cycloalkyl;
$R^2$ and $R^3$ taken together form
1) a 5-7 membered azacycle with the nitrogen atom to which they are attached and may include another nitrogen atom as one of the members and may be substituted with one or two substituents selected from
a) $C_{1-3}$ alkyl, and
b) $-NCH_2CF_3$; or
2) a 6-10 membered azabicycle;
$R^4$ is
1) $C_{1-5}$ alkyl, either unsubstituted or substituted with phenyl, or
2) phenyl; and
$R^5$ is
1) hydrogen or
2) $C_{1-3}$ alkyl.

Specific representative compounds are those included in the following table:

| $R^1$ | $R^2$ | $R^3$ | $R^4$ | $R^5$ |
|---|---|---|---|---|
| 3-CF3-phenyl | —(CH2)6— | | —CH3 | H |
| 3,5-dimethylphenyl | —CH3 | cyclohexyl | n-Pr— | H |

-continued
| R¹ | R² | R³ | R⁴ | R⁵ |
|---|---|---|---|---|
| 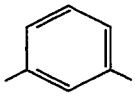 | | —(CH₂)₆— | n-Pr— | H |
| 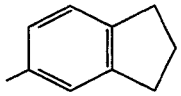 | | —(CH₂)₆— | —CH₃ | H |
| 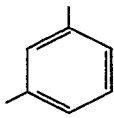 | | —(CH₂)₂—CH—(CH₂)₂—<br>　　　　　\|<br>　　　　　CH₃ | —CH₃ | H |
| 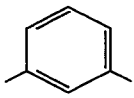 | | —(CH₂)₂—C—(CH₂)₂—<br>　　　　\| \|<br>　　　CH₃ CH₃ | —CH₃ | H |
| 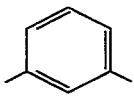 | | —CH₂—CH<cyclopentyl>CHCH₂— | —CH₃ | H |
| 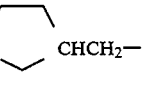 | | —CH₂—CH<cyclohexyl>CHCH₂— | —CH₃ | H |
| 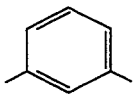 | —CH₃ | cyclohexyl | —CH₃ | H |
| 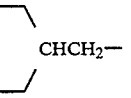 | | —(CH₂)₂—CH—(CH₂)₂—<br>　　　　　\|<br>　　　　　CH₃ | —CH₃ | H |
| 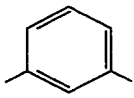 | | —(CH₂)₂—C—(CH₂)₂—<br>　　　　\| \|<br>　　　CH₃ CH₃ | —CH₃ | H |
| 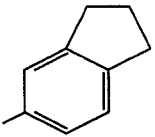 | | —(CH₂)₂—CH—(CH₂)₂—<br>　　　　　\|<br>　　　　　HN—CF₃ | n-C₃H₇ | H |
| 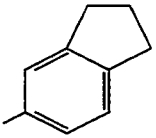 | | —(CH₂)₂—CH—(CH₂)₂—<br>　　　　　\|<br>　　　　　CH₃ | iso-C₄H₉ | H |
| 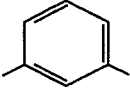 | | —(CH₂)₂—CH—(CH₂)₂—<br>　　　　　\|<br>　　　　　CH₃ | n-C₃H₇ | H |

-continued

| $R^1$ | $R^2$ | $R^3$ | $R^4$ | $R^5$ |
|---|---|---|---|---|
| indanyl (methyl-indane) group | | $-(CH_2)_2-CH(CH_3)-(CH_2)_2-$ | n-$C_3H_7$ | H |
| 3-fluorophenyl group | | $CH_2-CH\langle cyclopropane \rangle CH-CH_2$ | $-CH_3$ | H |
| 3-methylphenyl group | | cycloheptyl | $-CH_3$ | H |

The pharmaceutically acceptable salts of the compounds of Formulas I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, suffamic, phosphoric, nitric and the like; and the salts prepared from organic acids such as acetic, propionic, succinic, glycolic, stearic, lactic, malic, tartaric, citric, aseorbic, pamoic, maleic, hydroxymaleie, phenylacetic, glutamic, benzoic, salicyclic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometfic amounts or with an excess of the desired salt-forming inorganic or organic acid or base in a suitable solvent or various combinations of solvents.

The compounds useful in the novel method of treatment of the present invention, have the pharmacological properties required for the antiarrhythmic agents of Class III, namely the prolongation of the myocardial action potential in vitro, without a significant depression of the Vmax, and the prolongation of QTc-interval in anesthetized dogs.

These compounds are effective in treating and preventing all types of arrhythmias including ventricular and atrial (supraventricular) arrhythmias. The compounds of the present invention are especially useful to control reentrant arrhythmias and prevent sudden death due to the ventricular fibrillation. These compounds are also effective in treating and preventing impaired cardiac pump functions.

In the novel method of this invention of treating arrhythmia, one of the compounds or pharmaceutically acceptable salt thereof, is administered in an amount ranging from about 0.0001 to about 20 mg per kg of body weight per day, preferably from about 0.001 to about 10 mg per kg of body weight per day in a single dose or in 2 to 4 divided doses.

These compounds can be administered as the sole active ingredient or in combination with other antiarrhythmic agents or other cardiovascular agents.

These compounds, or pharmaceutically acceptable salts thereof, in She described dosages, are administered orally, intraperitoneally, subcutaneously, intramuscularly, transdermally, sublingually or intravenously. They are preferably administered intravenously or orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

The activity of the compounds described herein as antiarrhythmic agents is measured by their ability to block the IKs and IKr as determined by the following test protocol.

Outward potassium currents are measured in single guinea pig ventricular myocytes using a whole-cell voltage clamp technique described in detail elsewhere (Sanguinetti and Jurkiewicz, 1990. Two components of cardiac delayed actifier K+ current: differential sensitivity to block by Class III antiarrhythmic agents. J. Gen Physiol. 96: 195–215). Myocytes are isolated by enzymatic (collagenase and protease) digestion of Langandorf perfused hearts. Single cells are then voltage clamped using 1 mm square-bore pipettes filled with 0.5M Kgluconate, 25 mM KCl, 5 mM K(2)ATP. Cells are bathed in a solution containing, in mN: 132 NaCl, 4KCl, 1.2 MgCl[2], 10 HEPES, 10, glucose: pH 7.2, temp. 35° C.

Each cell is maintained at a holding potential of −50 mV. Test depolarizations are applied as voltage ramps from −85 to −50 mV, and as steps to −10 mV (0.5 s) and +50 mV (1.0 s). I[KI] is measured as peak outward current during the voltage ramp. I[Kr] is measured as tail currents upon repolarization from −10 mV to −50 mV. I[KS] is measured as time-dependent current during the pulse to +50 mV. Currents are measured during control, then after exposure to drug at two different concentrations.

Employing this test the compounds described herein have an IC$_{50}$ of less than 1000 nM as IKs and/or IKr blockers.

EXAMPLE 1

N-[3(R,S)-5-(N-Cyclohexyl-N-methylamino)-2,3-dihydro-2-oxo-1-propyl-1H-1,4-benzodiazepin-3-yl]1-N'-[3-methylphenyl]urea.

Step A: Preparation of 5-(N-Cyclohexyl-N-methylamino)-2-oxo-1-propyl-1,4-benzodiazepine To a solution of 2,5-dioxo-1-propyl-1,4-benzodiazepine (see Example 8) (10.0 g, 0.046 mol) in dichloromethane (200 ml) was added phosphorus pentachloride (11.5 g, 0.055 mol) in dichloromethane (400 ml) over 30 minutes. The reaction mixture was stirred at room temperature for 2 h then the solvent was removed under vacuum and the resulting oil was dried under high vacuum. The oil was redissolved in dichloromethane (200 ml) and a solution of N-methylcyclohexylamine (15.6 g, 0.138 mol) in dichloromethane (125 ml) was added dropwise. When the addition was complete, the reaction mixture was allowed to stir for 18 hours. The solution was washed with saturated sodium hydrogen carbonate solution (100 ml), and the aqueous layer was reextracted with dichloromethane (2×100 ml). The combined organic layers were washed with brine (100 ml), dried (sodium sulphate), filtered and concentrated in vacuo. The residue was dissolved in a small amount of dichloromethane and purified by flash column chromatography, eluted with 2% methanol/0.5% 0.88 ammonia solution/dichloromethane (3 litres) then 5% methanol/0.5% 0.88 ammonia solution/dichloromethane. Yield=15.8 g (quantitative), as a brown oil. $^1$H NMR (DMSO)δ0.68 (3H, t, J=7.3 Hz), 1.84–2.04 (3H, m), 2.72 (3H, s), 3.40 (1H, d, J=12.2 Hz), 3.54 (1H, m), 3.88 (1H, d, J= 12.2 Hz), 4.22 (1H, m), 7.34 (1H, m), 7.50 (1H, d, J=7.43 Hz), 7.60 (2H, m).

Step B: Preparation of 5-(N-Cyclohexyl-N-methylamino)-3-oximino-2-oxo-1-propyl-1,4-benzodiazepine The product from step (A) (5 g, 0.016 mol) was dissolved in dry toluene (500 ml) and cooled to −20° C. under an atmosphere of nitrogen. Potassium t-butoxide (8.59 g, 0.080 mol) was added followed after 30 minutes by the dropwise addition of isoamyl nitrite (2.36 ml, 0.0176 mol). The reaction mixture was stirred at −20° C. for 18 hours. The reaction was quenched by the addition of water (50 ml) and the mixture was neutralized to pH 7.4 by the addition of 1M hydrochloric acid. The solvents were removed in vacuo, the resulting solid was resuspended in dichloromethane and absorbed onto silica. The product was purified using flash silica chromatography, eluting with 0.5% 0.88 ammonium solution/2% methanol/dichloromethane followed by chromatography on an alumina column, eluting with 2% methanol/dichloromethane followed by 5% methanol/dichloromethane. Yield—2.31 g (42%) as a pale yellow foam. $^1$H NMR (DMSO)δ0.52–2.06 (16H, m), 2.60–2.92 (3H, m), 3.60 (1H, m), 4.26 (1H, m), 7.22–7.66 (14H, m), 9.84 and 10.02 (1H, 2×s).

Step C: Preparation of N-[3(RS)-5-(N-Cyclohexyl-N-methylamino)-2,3-dihydro-2-oxo-1-propyl-1H-1,4-benzodiazepin-3-yl]-N'-[3-methylphenyl]urea The product from step (B) (2.31 g, 0.0068 mol) was dissolved in acetic acid (40 ml), with activated zinc (8.83 g, 0.135 mol) and trifluoroacetic acid (5.21 ml, 0.067 mol). The reaction was heated at 40° C. for 8 h with vigorous stirring, then cooled to room temperature, filtered through hiflo, and washed through with acetic acid (2×20 ml). The solvent was removed in vacuo, the resulting oil was azeotroped with toluene and dried under high vacuum for 30 min to give a yellow foam. The foam was redissolved in tetrahydrofuran (50 ml), and triethylamine (1.0 ml, 0.0074 mol) was added followed by m-tolylisocyanate (0.87 ml, 0.0068 mol). The reaction was stirred at room temperature for 2 h then concentrated under vacuum. The residue was redissolved in dichloromethane (100 ml), washed with saturated sodium hydrogen carbonate solution (100 ml), separated and the aqueous phase was reextracted with dichloromethane (2×25 ml). The combined organic layers were washed with brine (50 ml), dried (sodium sulphate) and the solvent was removed in vacuo to give a dark blue solid. The solid was redissolved in methanol and absorbed onto flash silica. The product was purified by flash coltann chromatography with 0.5% 0.88 ammonia solution/dichloromethane as the eluent on a Lobar column. The product was isolated as a yellow solid, yield=0.25 g (8%). Mpt=118° C. (uncorr); $^1$H NMR (DMSO)δ0.70 (3H, t, J=7.4 Hz), 0.90–1.90 (13H, m), 2.23 (3H, s), 2.68 (3H, s), 3.64 (1H, m), 4.26 (1H, m), 4.90 (1H, d, J=8.4 Hz), 6.71 (1H, d, J=8.0 Hz), 6.92 (1H, d, J=8.6 Hz), 7.12 (2H, m), 7.16 (1H, s), 7.38 (1H, m), 7.51 (1H, d, J=7.5 Hz), 7.64 (2H, m); MS (CI) m/e 462 [MH]+. Anal. Found C, 66.38; H, 7.72; N, 14.07. $C_{27}H_{35}N_5O_2 \cdot 1.5H_2O$, requires C, 66.37; H, 7.84; N, 14.33%.

EXAMPLE 2

(−)-N-[5-(N-Cyclohexyl-N-methylamino)-2,3-dihydro-2-oxo-1-propyl-1H-1,4-benzodiazepin-3-yl]-N'-[3-methylphenyl]urea

Step A:

The racemate (430 mg) of Example 1 was separated using preparative chiral HPLC with a dinitrobenzoyl leucine column (250×20 m m i.d. 5 gm) using 94:5:1 1-chlorobutane:methanol:acetic acid as the mobile phase (with a flow rate of 20 ml/min and UV detection at 330 nM). The two enantiomers were efficiently separated into Peak A (eluted tint) and peak B (eluted second).

Step B:

Peak A from pan (A) was evaporated in vacuo, and was partitioned between dichloromethane and sodium carbonate solution. The organic phases were dried (MgSO$_4$), evaporated in vacuo and the residue obtained was triturated with diethyl ether and the resulting solid was collected by filtration to give:

Peak A (127 mg). Mp=121°–123° C.; $^1$H NMR (360 MHz, D$_6$-DMSO)δ0.69 (3H, t, J=7.4 Hz), 0.9–1.90 (13H, m), 2.21 (3H, s), 2.66 (3H, s), 3.64 (1H, m), 4.25 (1H, m), 4.89 (1H, d, J=8.4 Hz), 6.70 (1H, d, J=8.0 Hz), 6.94 (1H, d, J=7.5 Hz), 7.10 (2H, m), 7.16 (1H, s), 7.37 (1H, m), 7.50 (1 H, d, J=7.5 Hz), 7.65 (2H, m), 8.80 (1H, s); MS (CI) m/e 462 [MH]+. Anal. Found. C, 68.38; H, 7.74; N, 14.29. $C_{27}H_{35}N_5O_2 \cdot 0.85 H_2O$ requires C, 68.00; H, 7.76; N, 14.69. [α]$^{22}$D −114° (C=0.1, MeOH). Purity A:B=>99%.

EXAMPLE 3

(+)-N-[5-(N-Cyclohexyl-N-methylamino)-2,3-dihydro-2-oxo-1-propyl-1H-1,4-benzodiazepin-3-yl]-N'-[3-methylphenyl]urea Peak B from Example 2 was treated in the same way as Peak A Example 2 part b to afford the required product as a solid (62 mg). Mp=126°-127° C.; $^1$H NMR (360 MHz, D$_6$-DMSO)δ0.69 (3H, t, J=7.4 Hz), 0.9–1.90 (13H, m), 2.21 (3H, s), 2.66 (3H, s), 3.62 (1H, m), 4.25 (1H, m), 4.89 (1H, d, J=8.4Hz), 6.70 (1H, d, J=8.0 Hz), 6.94 (1H, d, J=7.5 Hz), 7.00 (2H, m), 7.17 (1H, s), 7.38 (1H, m), 7.50 (1H, d, J=7.5 Hz), 7.65 (2H, m), 8.80 (1 H, s); MS (CI) m/e 462 [MH]+. Anal. Found. C, 69.93; H, 7.54; N, 14.62. $C_{27}H_{35}N_5O_2$.0.2 H$_2$O requires C, 69.71; H, 7.67; N, 15.05% [α]$^{22}$D+108° (C=0.1, MeOH). Purity B:A=>96.4.

EXAMPLE 4

N-[3(RS)-5-(N-Cyclohexyl-N-methylamino)-2,3-dihydro-1-methyl-2-oxo-1H-1,4-benzodiazepin-3-yl]-N'-[3-methylphenyl]urea

Step A: Preparation of Methyl-2-(N-bromoacetyl-N-methylamino) benzoate

A solution of bromoacetyl bromide (209 g, 1.03 mol) in dichloromethane (200 ml) was added dropwise to a cooled (ice bath) solution of methyl N-methylanthranilate (158 g, 0.96 mol) in dichloromethane (1.4l). A solution of sodium hydroxide (59 g, 1.47 mol) in water (400 ml) was added dropwise to this ice cold solution then after addition the reaction mixture was stirred at room temperature for 20 hours. The organic phase was separated and washed with 1M hydrochloric acid (500 ml), brine (300 ml), saturated sodium hydrogen carbonate solution (400 ml), dried (sodium sulphate) then evaporated to afford the required product as a solid (255 g, 92%). $^1$H NMR (360 MHz, CDCL$_3$)δ3.23 (3H, s), 3.54 (1H, d, J=11 Hz), 3.60 (1H, d, J=11 Hz), 3.90 (3H, s), 7.40 (1H, d, J=8 Hz), 7.51 (1H, dd, J$_1$=J$_2$=8 Hz), 7.65 (1H, dd, J$_1$=J$_2$=8Hz), 8.04 (1 H, d, J=8 Hz).

Step B: Preparation of 2,5-Dioxo-1-methyl-1,4-benzodiazepine

Ammonia gas was bubbled through an ice-cooled solution of methyl 2-(N-bromoacetyl-N-methylamino)benzoate (255 g, 0.89 mol) in methanol (1.6l) until saturated. The cooling bath was removed and the reaction mixture left standing at room temperature for 18 hours. The precipitate was collected to afford the required product (79 g). The filtrate was evaporated and the residue partitioned between as dichloromethane (300 ml) and 10% citric acid solution (200 ml). The organic layer was separated, washed with brine (200 ml), dried (sodium sulphate) then evaporated to give a solid which was recrystallized from dichloromethane/petroleum ether (60–80) to afford further product (32.5 g). Total yield=111.5 g (73%). Mp 190°-193° C. $^1$H NMR (360 MHz, CDCl$_3$)δ3.42 (3H, s), 3.80 (2H, broad s), 6.80 (1H, s), 7.24 (1H, d, J=8 Hz), 7.32 (1H, dd, J$_1$=J$_2$=8 Hz), 7.57 (1H, dd, J$_1$=J$_2$=8 Hz), 7.90 (1H, d, J=8 Hz). Found C, 63.20; H, 5.25; N, 14.77. $C_{10}H_{10}N_2O_2$ requires C, 63.15; H, 5.30; N, 14.73%.

Step C:

The desired product was prepared as for Example 1 parts a, b, and c, using 2,5-dioxo-1-methyl-1,4-benzodiazepine in place of 2,5-dioxo-1-propyl-1,4-benzodiazepine to give a white solid which was recrystallized from methanol, water to give the desired product (70 mg). Mp 145°-147° C. $^1$H NMR (360 MHz, D$_6$-DMSO) δ0.99 (10H, m), 2.21 (3H, s), 2.65 (3H, s), 3.31 (4H, m), 4.92 (1H, d, J=8.4 Hz), 6.70 (1H, d, J=8.0 Hz), 6.93 (1H, d, J=7.5 Hz), 7.09 (2H, m), 7.17 (1H, s), 7.36 (1H, m), 7.49–7.69 (3H, m), 8.80 (1H, s); MS (CI) m/e 434 [MH]+. Anal. Found C, 67.22; H, 7.23; N, 15.29. $C_{25}H_{31}N_5O_2$.0.75 H$_2$O requires C, 67.17; H, 7.33; N, 15.67%.

EXAMPLE 5

(−)-N-[5-(N-Cyclohexyl-N-methylamino)-2,3-dihydro-2-oxo-1-methyl-1H-1,4-benzodiazepin-3-yl]-N'-[3-methylphenyl]urea Hydrochloride The desired product was separated from the racemate of Example 4 by chiral HPLC as for Example 2, Step A. Peak A (eluted first) was treated as for Example 2 part B and the free base obtained was dissolved in dichloromethane. Ethereal hydrogen chloride was added and after 5 minutes the solvent was removed in vacuo. The resulting oil was crystallized from dichlromethane/ether to give the desired hydrochloride as a white solid (100 mg). Mp 193°–195° C. $^1$H (360 MHz, D$_6$-DMSO, trifluoroacetic acid)δ0.95–1.95 (10H, m), 2.23 (3H, s), 3.12 (3H, s), 3.43 (4H, m), 5.39 (1H, m), 6.76 (1H, d, J=7.2 Hz), 7.11–7.90 (7H, m). MS (CI) m/e [MH]+. Anal. Found. C, 60.45; H, 7.02; N, 14.05. $C_{25}H_{31}N_5O_2$.HCl 1.5 H$_2$O requires C, 60.41; H, 7.02; N, 14.35%, [α]$^{22}$D−195° (c=0.1, MeOH). Purity A:B=>99%.

EXAMPLE 6

(+)-N-[5-(N-Cyclohexyl-N-methylamino)-2,3-dihydro-2-oxo-1-methyl-1H-1,4-benzodiazepin-3-yl]-N'-[3-methylphenyl]urea Hydrochloride The desired product was separated from the racemate from Example 4 by chiral HPLC as for Example 2 part A. Peak B (eluted second) was treated as for Example 5 peak A to yield the desired hydrochloride (90 mg). Mp 194°–196° C. $^1$H NMR (360 MHz, D$_6$-DMSO+trifluoroacetic acid)δ0.95–1.95 (10H, m), 2.24 (3H, s), 3.12 (3H, s), 3.43 (4H, m), 5.39 (1H, m), 6.76 (1H, d, J=7.5 Hz), 7.06–7.86 (7H, m), 9.20 (1H, s); MS (CI) m/e 434 [MH]+. Anal. Found. C, 58.28; H, 6.82; N, 13.47. $C_{25}H_{31}N_5O_2$.HCl.2.35 H$_2$O requires C, 58.61; H, 7.22; N, 13.67%. [α]$^{22}$D+154° (C=0.1, MeOH). Purity B:A=>95%.

EXAMPLE 7

N-[3(R,S)-2,3-Dihydro-1-methyl-2-oxo-5-(4-methylpiperidin-1-yl)-1H,1,4-benzodiazepin-3-yl]N'-[3-methylphenyl]urea

Step A: 5-Chloro-1,2-dihydro-1-methyl-3H-1,4-benzodiazepin-2-one hydrochloride A solution of phosphorus pentachloride (1.2 g) in dichloromethane (50 ml) was added dropwise to a solution of 1-methyl-1,2,3,4-tetrahydro-3H-1,4-benzodiazepin-2,5-dione (0.9 g) in dichloromethane (20 ml) stirring at room temperature. After 2 h the solvent was evaporated and the volatiles azeotropically distilled with toluene to afford product as an orange foam which was not purified further.

Step B:
1,2-Dihydro-1-methyl-5-(4-methylpiperidin-1-yl)-3H-1,4-benzodiazepin-2-one 4-Methyl piperidine (1.56 g) was added to a solution of crude 5-chloro-1,2-dihydro-1-methyl-3H-1,4-benzodiazepin-2-one hydrochloride (0.005 mol) in dichloromethane (50 ml) cooled in ice. After warming to room temperature, sodium bicarbonate solution (20 ml) was added. The organic phase was separated, dried ($Na_2SO_4$) and evaporated to give an orange oil which was purified by column chromatography on silica with $CH_2Cl_2 \Delta CH_2Cl_2$:MeOH 95:5 as eluant to afford product.

Step C:
1,2-Dihydro-1-methyl-3-oximido-5-(4-methylpiperdin-1-yl)-3H-1,4-benzodiazepin-2-one Potassium t-butoxide (0.65 g) was added portionwise to a solution of 1,2-dihydro-1-methyl-5-(4-methylpiperidin-1-yl)-3H-1,4-benzodiazepin-2-one (0.64 g) in dry toluene (50 ml) cooled below $-10°$ C., under nitrogen. After 15 min isoamyl nitrite (0.33 ml) was added in one portion and stirring continued for 25 min. Citric acid (1M, 20 ml) was then added and the mixture extracted with ethyl acetate (4×50 ml). The combined organic phase was washed with water, dried ($Na_2SO_4$) and evaporated to give a gummy solid which was triturated with diethyl ether to give product.

mp 225°–228° C. $^1$H NMR (360 MHz, $D_6$-DMSO)δ0.90–1.15 (4H, m), 1.20–1.36 (1H, m), 1.54–1.76 (3H, m), 2.77–3.01 (2H, m), 3.26 (3H, s), 3.69–4.24 (2H, m), 7.24–7.32.

Step D:
3-Amino-1,2-dihydro-1-methyl-5-(4-methylpiperidin-1-yl )-3H-1,4-benzodiazepin-2-one A suspension of 1,2-dihydro-1-methyl-3-oximino-5-(4-methylpiperidin-1-yl)-3H-1,4-benzodiazepin-2-one (0.27 g) and 5% ruthenium on carbon (0.16 g) in methanol (50 ml) was hydrogenated at 55 psi $H_2$ at 70° for 24 h. The catalyst was then removed by filtration and the solvent evaporated. The residue was purified by filtration and the solvent evaporated. The residue was purified by column chromatography on silica with $CH_2Cl_2$:MeOH 98:2Δ9:1 as eluant to afford product.

Step E: N-[3(R,S)-2,3 Dihydro-1-methyl-2-oxo-5-(4-methylpiperidin-1-yl)-1H-1,4-benzodiazepin-3-yl]N'-(3-methylphenyl)urea m-Tolyl isocyanate (0.26 ml) was added in one portion to a solution of 3-amino-1,2-dihydro-1-methyl-5-(4-methylpiperidin-1-yl)-3H-1,4-benzodiazepin-2 -one (0.57 g) in THF (16 ml) at room temperature. Following the procedure of Example 1, Step C, the product was obtained. After recrystallization from methanol it had mp 142° C. (dec.). $^1$H NMR (360 MHz, $CDCl_3$)δ0.95 (3H, d, J=6.3 Hz), 1.06–1.19 (1H, m), 1.24–1.36 (1H, m), 1.46–1.60 (2H, m), 1.65–1.76 (1H, m), 2.28 (3H, s), 2.62–2.82 (2H, m), 3.41 (3H, s), 3.48–3.58 (1H, m), 3.90–3.98 (1H, m), 5.28 (1H, d, J=8.6 Hz), 6.54 (1H, d, J=7.9 Hz), 6.82 (1H, d, J=7.3 Hz), 6.95 (1H, s), 7.04–7.16 (2H, m), 7.21–7.32 (3H, m), 7.45–7.56 (2H, m). MS (CI)m/e 420 [MH]+ Anal. Found C, 65.09; H, 6.79; N, 15.94. $C_{24}H_{29}N_5O_2$.1.25 ($H_2O$) requires C, 65.21; H, 7.18; N, 15.84%.

EXAMPLE 8
N-[3(R,S)-2,3-Dihydro-5-(4-methylpiperazin-1-yl)-2-oxo-1-propyl-1H-1,4-benzodiazepin-3-yl]N'-[3-methoxyphenyl]urea

Step A: Methyl N-propyl anthranilate

To a stirred solution of methyl anthranilate (10.0 g) in methanol (50 ml) was added propionitrile (4.77 ml) followed by glacial acetic acid (20 ml). Sodium cyanoborohydride (4.5 g) was added in portions over 30 minutes, maintaining the temperature below 30° C. After addition the reaction mixture was stirred for 2 hours. The solvents were evaporated in vacuo and the residue partitioned between ethyl acetate (50 ml) and 10% potassium carbonate solution (100 ml). The organic layer was separated and the aqueous re-extracted with ethyl acetate (2×50 ml). The combined organics were washed with brine, dried (sodium sulphate) then evaporated to give a yellow oil which was distilled under vacuum. The title product was obtained as a pale yellow oil (10.6 g), bp 138°–140° C. (0.3 mmHg). $R_f$0.65 in ethyl acetate/n-hexane (1:1) on silica plates. $^1$H NMR (360 MHz, $CDCl_3$)δ1.03 (3H, t, J=7 Hz), 1.71 (2H, sextet, J=7 Hz), 5:15 (2H, q, J=7 Hz), 5.85 (3H, s), 6.56 (1H, dd, $J_1=J_2=8$ Hz), 6.67 (1H, d, J=8 Hz), 7.34 (1H, ddd, $J_1=J_2=8$ Hz, $J_3=8$ Hz), 7.69 (11t, broad resonance), 7.88 (1H, dd, $J_1=3$ Hz, $J_2=8$ Hz). Found: C, 66.79; H, 7.62; N, 7.33. $C_{11}H_{15}NO_2$.0.25 $H_2O$ requires C, 66.81; H, 7.90; N, 7.08%.

Step B:
1-Propyl-1,2,3,4-tetrahydro-3H-1,4-benzodiazepin-2,5-dione

Prepared from methyl-N-propyl anthranilate using the method described in Example 4, Step A & B. m.p. 137°–138° C. $R_f$0.20 in ethyl acetate/petroleum ether (60–80) (1:1) on silica plates. MS, CI+, m/z=219 for $(M+H)^+$.

Step C:
N-[3(R,S)-2,3-Dihydro-5-(4-methylpiperazin-1-yl)-2-oxo-1-propyl-1H-1,4-benzodiazepin-3-yl]-N'-[3-methoxyphenyl]urea The title compound was prepared from the product of Step B as described in Example 1, Step A to C, substituting 3-methoxyphenyl isocyanate for 3-methylphenyl isocyanate; m.p. 180° C. (dec.). $R_f$ 0.30 in 10% methanol/dichloromethane on silica plates. Found: C, 61.30; H, 6.98; N, 16.87. $C_{25}H_{32}N_6O_3$.1.5 $H_2O$ requires C, 61.08; H, 7.18; N, 17.10%.

EXAMPLE 9
N-[3(R,S)-2,3-Dihydro-5-(4-ethylpiperazin-1-yl)-1-(2-methylpropyl)-2-oxo-1H-1,4-benzodiazepin-3-yl]-N'-[3-methylphenyl]urea

Step A: Methyl N-(2-methylpropyl)anthranilate

The title compound was obtained from methyl anthranilate and isobutyraldehyde as described in Example 8. bp 145° C. (0.3 mmHg) (Kugelrohr). $R_f$0.75 in ethyl acetate/n-hexane (1:1) on silica plates.

Step B:
1-(2-Methylpropyl-1,2,3,4-tetrahydro-3H-1,4-benzodiazepin-2,5-dione.

Prepared from methyl N-(2-methylpropyl)anthranilate using the method described in Example 4. m.p.

176°–178° C. dichloromethane/diethyl ether). Found: C, 67.35; H, 6.74; N, 12.13. $C_{13}H_{16}N_2O_2$ requires C, 67.22; H, 6.94; N, 12.06%.

Step C:
1,2-Dihydro-5-(4-methylpiperazin-1-yl)-1-(2-methylpropyl)-3H-1,4-benzodiazepin-2-one Prepared from 1-(2-methylpropyl)-1,2,3,4-tetrahydro-3H-1,4-benzodiazepin-2,5-dione and N-methylpiperazine using the method described in Example 1 (Step A). m.p. 134°–136 ° C. (dichloromethane/diethyl ether). Found: C, 68.98; H, 8.40; N, 17.92. $C_{18}H_{26}N_4O$ requires C, 68.76; H, 8.33; N, 17.82%.

Step D:
N-[3(R,S)-2,3-Dihydro-5-(4-methylpiperazin-1-yl)-1-(2-methylpropyl)-2-oxo-1H-1,4-benzodiazepin-3-yl]-N'-[3-ethylphenyl]urea The title compound was obtained with 3-ethylphenyl isocyanate and the product from Step C using the procedures described in Example 1 (Steps B–C); m.p. 223°–224° C. (ethyl acetate/n-hexane). $R_f$ 0.36 in 10% methanol/dichloromethane on silica plates. Found: C, 68.44; H, 7.64; N, 17.81. $C_{27}H_{36}N_6O_2$ requires C, 68.04; H, 7.61; N, 17.63%.

EXAMPLE 10

(−)-N-[2,3-Dihydro-5-(4-methylpiperazin-1-yl)-1-(2-methylpropyl)-2-oxo-1H,1,4-benzodiazepin-3-yl]-N'-[3-ethylphenyl]urea N-[3(R,S)-2,3-Dihydro-5-(4-methylpiperazin-1-yl)-1-(2-methylpropyl)-2-oxo-1H-1,4-benzodiazepin-3-yl]-N'-[3-ethylphenyl]urea (Example 9, 700 mg) was separated into its two enantiomers using a semi-preparative dinitrobenzoylleucine Pirkle column [(250×20) mm] eluting with 2% methanol in dichloromethane (including 0.8% acetic acid). Flow rate=20 ml/minute, U.V. detection at 280 nm. Analysis was performed on an analytical dinitrobenzoylleucine Pirkle column [(250×4.6 mm)] eluting with 3% methanol in dichloromethane (including 1% acetic acid). Flow rate=1 ml/minute, U.V. detection at 250 nm.

The free base was liberated and obtained as a cream powder (200 mg). HPLC $R_t$=3.43 minutes $[\alpha]^{23°}\,^C\!D = -59.5°$ (c=0.2, methanol). mp>113° C. (dec.).

EXAMPLE 11

(+)-N-[2,3-Dihydro-5-(4-methylpiperazin-1-yl)-1-(2-methylpropyl)-2-oxo-1H-1,4-benzodiazepin-3-yl]-N'-[3-ethylphenyl]urea The title compound was obtained (270 mg) using the procedure described in Example 10. HPLC $R_t$=5.61 minutes. $[\alpha]^{23°}\,^C\!D = +50.0°$ (c=0.2, methanol). mp>113° C. (dec.).

EXAMPLE 12

N-[3(R,S)-2,3-Dihydro-5-(4-methylpiperazin-1-yl)-2-oxo-1-propyl-1H-1,4-benzodiazepin-3-yl]-N'-[5-indanyl]urea Step A:
3-Amino-1,2-dihydro-5-(4-methylpiperazin-1-yl)-1-propyl-3H-1,4-benzodiazepin-2-one Trifluoroacetate 1,2-Dihydro-5-(4-methylpiperazin-1-yl)-3-oximido-1-propyl-3H-1,4-benzodiazepin-2-one (2.0 g) was dissolved in glacial acetic acid (35 ml). Trifluoroacetic acid (4.68 ml) was added and the solution warmed to 40° C. Activated zinc powder (Fieser and Fieser, 1967, Volume 1, 1276, 3.97 g) was added and the mixture was stirred at 40° C. for 5 hours. The mixture was cooled, filtered then evaporated to give the crude amine trifluoracetate salt, which was used in the next step.

Step B:
N-[3(R,S)-2,3-Dihydro-5-(4-methylpiperazin-1-yl)-2-oxo-1-propyl-1H-1,4-benzodiazepin-3-yl]-N'-[5-indanyl]urea Triphosgene (122 mg) was added to a stirred, cooled (4° C.) solution of 5-aminoindan (220 mg) in anhydrous tetrahydrofuran (10 ml). Triethylamine (0.175 ml) was added and the mixture was stirred at 4° C. for 20 minutes. 3-Amino-1,2-dihydro-1-propyl-5-(4-methylpiperazin-1-yl)-3H-1,4-benzodiazepin-2-one trifluoroacetate (650 mg crude) was suspended in anhydrous tetrahydrofuran (10 ml). Triethylamine (0.145 ml) was added and the resulting red solution was added to the pre-formed isocyanate at 4° C. After addition the cooling bath was removed and the mixture stirred at room temperature for 1 hour. The title compound was isolated and recrystallized from propan-2-ol to afford a colorless solid, m.p. 170°–171° C. (methanol). $R_f$ 0.30 in dichloromethane/methanol (9:1) on silica plates. $^1$H NMR (360 MHz, DCCl$_3$)δ0.77 (3H, t, J=7 Hz), 1.35–1.55 (2H, m), 2.0–2.1 (2H, m), 2.33 (3H, s), 2.3–2.4 (2H, m), 2.44–2.56 (2H, m), 2.8–2.9 (4H, m), 3.20–3.35 (4H, m), 3.50–3.58 (1H, m), 4.31–4.40 (1H, m), 5.24 (1H, d, J=8 Hz), 6.37 (1H, d, J=8 Hz), 6.44 (1H, s), 7.03 (1H, d, J=8 Hz), 7.13 (1H, d, J=8 Hz), 7.24–7.29 (2H, m), 7.35 (1H, d, J=8 Hz), 7.46–7.55 (2H, m). MS, CI+, m/z=476. Found: C, 65.83; H, 7.37; N, 17.06. $C_{27}H_{34}N_6O_2\cdot H_2O$ requires C, 66.09; H, 7.16; N, 17.30%.

EXAMPLE 13

(−)-N-[2,3-Dihydro-5-(4-methylpiperazin-1-yl)-2-oxo-1-propyl-1H-1,4-benzodiazepin-3-yl]-N'[5-indanyl]urea Step A:
α-Amino-N-(2,3-dihydro-5-(4-methylpiperazin-1-yl-2-oxo-1-propyl-1H-1,4-benzodiazepin-3-yl)benzene propanamide To a stirred solution of 3-amino-1,2-dihydro-5-(4-methylpiperazin-1-yl)-1-propyl-3H-1,4-benzodiazepin-2-one (Example 12, 2.96 g) in anhydrous dimethylformamide (30 ml) was added BOC-D-phenylalanine (2.61 g), 1-hydroxybenzotriazole (1.33 g), 1-(3-dimethylaminopropyl)-3-ethyl-carbodiimide hydrochloride (1.89 g) and triethylamine (1.37 ml). After stirring at room temperature for 15 minutes the solution was treated with saturated sodium hydrogen carbonate solution then extracted with ethyl acetate (4×100 ml). The combined organics were washed with saturated sodium chloride solution, dried (sodium sulphate), evaporated to dryness and the resulting brown oil purified by column chromatography on silica using 5% methanol/dichloromethane to 10% methanol/dichloromethane. The product obtained (5.28 g) was treated at 0° C. with ethyl acetate (100 ml) saturated with hydrogen chloride gas and stirred at 0° C. for 1 hour. The solution was basified to pH=9 with saturated sodium hydrogen carbonate solution, the organic layer was separated and the aqueous re-extracted with ethyl acetate (4×100 ml). The combined organics were dried (sodium sulphate) and the more polar (by silica tlc) diastereomer crystallized from methanol/diethyl ether to afford a beige solid (460 mg). m.p. 152°–153° C. Rf 0.50 in dichloromethane/methanol/ammonia (9:1:0.1) on silica plates. HPLC (Spherisorb ODS2 column, 25% acetonitrile/75% of 0.2% triethylamine in water, pH to 3 with orthophosphoric acid): $R_t$ 5.09 minutes, 99.5%. $^1$H NMR (360 MHz, DMSO-d$_6$)δ0.68 (3H, t, J=7 Hz), 1.20–1.29 (1H, m), 1.37–1.44 (1H, m), 2.19 (3H, s), 2.25–2.35 (2H, m), 2.40–2.48 (2H, m), 2.59 (1H, dd, $J_1$=9, $J_2$ =13 Hz), 3.00 (1H, dd, $J_1$=4, $J_2$13 Hz), 3.10–3.30 (4H, m), 3.47 (1H, dd, $J_1$=4 Hz, $J_2$=9 Hz), 3.60–3.68 (1H, m), 4.19–4.28 (1H, m), 4.97 (1H, d, J=8 Hz)m, 7.16–7.30 (5H, m), 7.36-7.42 (1H, m), 7.55 (1H, d, J=8 Hz), 7.63–7.66 (2H, m), 8.76 (1H, d, J=8 Hz). Found: C, 67.62; H, 7.24; N, 18.17. $C_{26}H_{34}N_6O_2$ requires 67.51: H, 7.41; N, 18.17%.

Step B:

(−)-N-[2,3-Dihydro-5-(4-methylpiperazin-1-yl)-2-oxo-1-propyl-1H-1,4-benzodiazepin-3-yl]-N'-[5-indanyl]urea Phenyl isothiocyanate (117 μl) was added to a stirred solution of the foregoing diastereomeric amide (0.41 g) in anhydrous dichloromethane (20 ml) then heated at 40° C. for 3 hours. The reaction mixture was evaporated and the residue purified by column chromatography on silica using dichloromethane to dichloromethane/methanol/ammonia (20:1:0.1), gradient elution, to afford the thiourea (0.53 g). Trifluoroacetic acid (20 ml) was added to the solid thiourea (0.53 g) and the mixture was stirred at room temperature for 40 minutes. The mixture was evaporated to dryness, the residue dissolved in water (50 ml), washed with diethyl ether (20 ml) then the aqueous was freeze dried and azeotroped with toluene to afford the homochiral amine trifluoroacetate (0.54 g) which was used crude.

(−)-N-[2,3-Dihydro-5-(4-methylpiperazin-1-yl)-2-oxo-1-propyl-1H-1,4-benzodiazepin-3-yl]-N'-[5-indanyl]urea was obtained (170 mg) from the foregoing homochiral amine free base (obtained from the trifluoroacetate salt), 5-aminoindan and triphosgene as described in Example 12, Step B, ensuring the mixture was at pH=9. mp>152° C. HPLC (Spherisorb ODS2 column, 50% acetonitrile/50% of 0.2% triethylamine in water, pH to 3 with orthophosphoric acid): $R_t$ 6.9 minutes, >99%, Chiral HPLC (Pirkle dinitrobenzoylleucine column, 3% methanol in dichloromethane (containing 1% acetic acid)): 98.6% ee. $[\alpha]^{23}$ $^C$D=−71.5° (c=0.2, methanol). Found: C, 68.25; H, 7.16; N, 17.85. $C_{27}H_{34}N_6O_2$ requires C, 68.33; H, 7.22; N, 17.71%.

EXAMPLE 14

N-[3(R,S)-2,3-Dihydro-7-methyl-5-(4-methylpiperazin-1-yl)-2-oxo-1-propyl-1H-1,4-benzodiazepin-3-yl]-N'-[3-methylphenyl]urea The title compound was obtained from methyl 5-methylanthranilate, m.p. 62° C. (water), using the procedures described in Examples 8; m.p. 127°–130° C. MS, m/z=462 for M+. $^1$H NMR (360 MHz, DMSO-d$_6$)δ0.68 (3H, t, J=7 Hz), 1.14–1.40 (2H, m), 2.19 (3H, s s), 2.22 (3H, s), 2.24–2.48 (7H, m), 3.04-3.24 (4H, m), 3.58–3.62 (1H, m), 4.20–4.25 (1H, m), 4.92 (H, d, J=8 Hz), 6.70 (1H, d, J=8 Hz), 7.02 (1H, d, J=8 Hz), 7.04–7.12 (2H, m), 7.16 (1H, s), 7.33 (1H, d, J=2 Hz), 7.46 (1H, dd, $J_1$=2, $J_2$=8 Hz), 7.54 (1H, d, J=8 Hz), 7.46 (1H, dd, J1=2, J2=8 Hz), 7.54 (1H, d, J=8 Hz), 8.80 (1H, s). Found: C, 65.74; H, 7.31; N, 17.64. $C_{26}H_{34}N_6O_2.0.7\ H_2O$ requires C, 65.72; H, 7.51; N, 17.69%.

EXAMPLE 15

N-[3(R,S)-2,3-Dihydro-5-(homopiperidin-1-yl)-1-methyl-2-oxo-1H-1,4-benzodiazepin-3-yl]-N'-[5-indanyl]urea The title Compound was obtained (145 mg) from 3-amino-1,2-dihydro-5-(homopiperidin-1-yl)-1-methyl-3H-1,4-benzodiazepin-2-one (prepared by procedures analagous to these of Example 7 Steps A–F) and 5-aminoindan as described in Example 12, Step B. m.p.>130° C. (dichloromethane). Rf 0.50 in dichloromethane/methanol (9:1) on silica plates. MS, CI+, m/z=446 for (M+H)+. $^1$H NMR (360 MHz, CDCl$_3$)δ1.40–1.80 (8H, m), 1.99–2.08 (2H, m), 2.80–2.87 (4H, m), 3.34–3.46 (7H, m), 5.24 (1H, d, J=8 Hz), 6.33 (1H, d, J=8 Hz), 6.74 (1H, s), 7.01 (1H, dd, $J_1$=2 Hz, $J_2$=8 Hz), 7.09 (1H, d, J=8 Hz), 7.20–7.32 (3H, m), 7.45–7.51 (2H, m). Found: C, 63.37; H, 6.43; N, 13.93. $C_{26}H_{31}N_5O_2.0.7CH_2Cl_2$ requires C, 63.50; H, 6.47; N, 13.87%

EXAMPLE 16

N-[3(R,S)-2,3-Dihydro-5-(homopiperidin-1-yl)-2-oxo-1-propyl-1H-1,4-benzodiazepin-3-yl]-N'-[3-methylphenyl]urea Step A:

1,2-Dihydro-5-(homopiperidin-1-yl)-1-propyl-3H-1,4-benzodiazepin-2-one

Carrying out Steps A of Example 1 using homopiperidine and 1-propyl-1,2,3,4-tetrahydro-3H-1,4-benzodiazepin-2,5-dione afforded the title compound as a pale yellow solid (10.5 g). m.p. 115°–118° C. The hydrochloride salt had m.p. 186°–188° C. (Ethyl Acetate). MS, CI+, m/z=300 for (M+H)+of free base. Found: C, 60.90; H, 7.79; 1 N, 11.79. $C_{18}H_{25}N_3O.HCl.H_2O$ requires C, 61.09; H, 7.97; N, 11.87 %.

Step B:

1,2-Dihydro-5-(homopiperidin-1-yl)-3-oximido-1-propyl-3H-1,4-benzodiazepin-2-one Carrying out Step B of Example 1 using the foregoing benzodiazepine and leaving the reaction mixture at −20° C. for 6 hours afforded the title compound as a cream solid (2.40 g). m.p. 163°–165° C. (Ethyl acetate/n-hexane). MS, CI+, m/z=329 for (M+H)+. Found: C, 65.66; H, 7.32; N, 16.87. $C_{18}H_{24}N_4O_2$ requires C, 65,83; H, 7.37; N, 17.06%.

Step C:

N-(3(R,S)-2,3-Dihydro-5-(homopiperidin-1-yl)-2-oxo-1-propyl-1H-1,4-benzodiazepin-3-yl]-N'-[3-methylphenyl]-urea The title compound was obtained from the foregoing oxime by procedures substantially as described in Example 1. Steps C and D; m.p. 190°–192° C. (ethyl acetate). Found: C, 69.57; H, 7.37; N, 15.53. $C_{26}H_{33}N_5O_2$ requires C, 69.77; H, 7.43; N, 15.65%.

EXAMPLE 17

N-[3(R,S)-2,3-Dihydro-5-(homopiperidin-1-yl)-1-methyl-2-oxo-1H-1,4-benzodiazepin-3-yl]-N'-[3-trifluoromethylphenyl]urea The title compound was obtained from 3-amino-1,2-dihydro-5-(homopiperidin-1-yl)-1-methyl-3H-1,4-benzodiazepin-2-one and 3-tfifluoromethylphenyl isocyanate as described in Example 1, Step C. m.p. 127°–130° C. (dichloromethane/diethyl ether). $R_f$ 0.70 in dichloromethane/methanol (9:1) on silica plates. MS, CI+, m/z 474 for (M+H)+. Found: C, 59.79; H, 5.48; N, 14.45. $C_{24}H_{26}F_3N_5O_2 \cdot 0.5H_2O$ requires C, 59.74; H, 5.64; N, 14.51%.

EXAMPLE 18

(−)-N-[2,3-Dihydro-5-(homopiperidin-1-yl)-1-methyl-2-oxo-1H-1,4-benzodiazepin-3-yl]-N'[5-indanyl]urea hydrochloride N-[3(R,S)-2,3-Dihydro-5-(homopiperidin-1-yl)-1-methyl-2-oxo-1H-1,4-benzodiazepin-3-yl]-N'-[5-indanyl]urea (Example 19, 2.6 g) was separated into its two enantiomers using a semi-preparative dinitrobenzoylleucine Pirkle column (5μ) [(250×20)mm] eluting with 3% methanol in 1-chlorobutane (including 1% acetic acid).

The free base was liberated and obtained as a colorless solid (840 mg). The hydrochloride salt had m.p. 195° C. (dec) (acetone/ethyl acetate (1:1)). Rf 0.62 in 10% methanol in dichloromethane on silica plates. $[\alpha]^{23°\ C.}D = -162.5°$ (c=0.2, methanol). Found: C, 62.87; H, 6.78; N, 14.00. $C_{26}H_{31}H_5O_2 \cdot HCl \cdot 0.75H_2O$ requires C, 63.02; H, 6.81; N, 14.13%.

EXAMPLE 19

(+)-N-(2,3-Dihydro-5-(homopiperidin-1-yl)-1-methyl--2-oxo-1H-1,4--benzodiazepin-3-yl]-N'-[5-indanyl]urea hydrochloride The title compound free base was obtained (900 mg) using the procedure described in Example 18. The hydrochloride salt had m.p. 195° C. (dec). Rf 0.62 in 10% methanol in dichloromethane on silica plates. $[\alpha]^{23°\ C.}D = +159°$ (c=0.2, methanol). Found: C, 62.81; s H, 6.86; N, 14.08. $C_{26}H_{31}N_5O_2 \cdot HCl \cdot 0.75H_2O$ requires C, 63.02; H, 6.81; N, 14.13%.

What is claimed is:

1. A method of treating arrhythmia in a patient in need of such treatment which comprises the administration of a therapeutically effective amount of a compound of structural formula I:

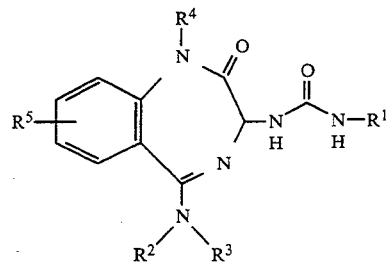

or a pharmaceutically acceptable salt thereof, wherein
$R^1$ is
  1) phenyl, either unsubtituted or substituted with one or two substituents selected from Cl, F, $CF_3$, $C_{1-3}$ alkyl and $C_{1-3}$ alkoxy,
  2) indan-5-yl;
$R^2$ and $R^3$ taken together form
  1) a 5–7 membered azacycle with the nitrogen atom to which they are attached and may include another nitrogen atom as one of the members and may be substituted with one or two substituents selected from
     a) $C_{1-3}$ alkyl, and
     b) —$NCH_2CF_3$; or
  2) a 6–10 membered azabicycle;
$R^4$ is 1) $C_{1-5}$ alkyl either unsubtituted or substituted with phenyl, or
  2) phenyl; and
$R^5$ is
  1) hydrogen or
  2) $C_{1-3}$ alkyl.

2. The method of claim 1 wherein the compound is selected from those in the following Table:

| $R^1$ | $R^2$ | $R^3$ | $R^4$ | $R^5$ |
|---|---|---|---|---|
| (3,5-dimethylphenyl) | —($CH_2$)$_6$— | | n-Pr— | H |
| (3,5-dimethylphenyl) | —($CH_2$)$_2$—CH—($CH_2$)$_2$—<br>$\quad\quad\quad\quad$ $CH_3$ | | —$CH_3$ | H |
| (3,5-dimethylphenyl) | —($CH_2$)$_2$—C—($CH_2$)$_2$—<br>$\quad\quad$ $CH_3$ $\;$ $CH_3$ | | —$CH_3$ | H |

-continued

| R¹ | R² | R³ | R⁴ | R⁵ |
|---|---|---|---|---|
| 3-methylphenyl | —CH₂—CH | CHCH₂— (cyclopentane) | —CH₃ | H |
| 3-methylphenyl | —CH₂—CH | CHCH₂— (cyclohexane) | —CH₃ | H |
| indanyl | —(CH₂)₂—CH(CH₃)—(CH₂)₂— | | —CH₃ | H |
| indanyl | —(CH₂)₂—C(CH₃)₂—(CH₂)₂— | | —CH₃ | H |
| 3-methylphenyl | —(CH₂)₂—CH[NH-CH₂CF₃]—(CH₂)₂— | | n-C₃H₇ | H |
| —(CH₂)₂—C(CH₃)₂—(CH₂)₂— | —(CH₂)₂—CH(CH₃)—(CH₂)₂— | | iso-C₄H₉ | H |
| 3-methoxyphenyl | —(CH₂)₂—CH(CH₃)—(CH₂)₂— | | n-C₃H₇ | H |
| indanyl | —(CH₂)₂—CH(CH₃)—(CH₂)₂— | | n-C₃H₇ | H |
| 3-fluorophenyl | —CH₂—CH | CHCH₂— (cyclopentane) | —CH₃ | H |

3. The method of claim 1 wherein the compound of formula I is administered in combination with another antiarrhythmic or cardiovascular agent.

4. A pharmaceutical formulation comprising a pharmaceutical carrier and an effective amount of the compound of formula I of claim 1 in combination with another antiarrhythmic or cardiovascular agent.

* * * * *